(12) United States Patent
Shusterman

(10) Patent No.: US 9,801,607 B2
(45) Date of Patent: Oct. 31, 2017

(54) EVALUATING ARTERIAL PRESSURE, VASOMOTOR ACTIVITY AND THEIR RESPONSE TO DIAGNOSTIC TESTS

(71) Applicant: Vladimir Shusterman, Pittsburgh, PA (US)

(72) Inventor: Vladimir Shusterman, Pittsburgh, PA (US)

(*) Notice: Subject to any disclaimer, the term of this patent is extended or adjusted under 35 U.S.C. 154(b) by 747 days.

(21) Appl. No.: 14/196,738

(22) Filed: Mar. 4, 2014

(65) Prior Publication Data

US 2014/0187941 A1    Jul. 3, 2014

Related U.S. Application Data

(63) Continuation-in-part of application No. 13/017,043, filed on Jan. 30, 2011, now Pat. No. 8,706,464.

(60) Provisional application No. 61/300,004, filed on Jan. 31, 2010.

(51) Int. Cl.
| | |
|---|---|
| *G01N 33/48* | (2006.01) |
| *A61B 8/04* | (2006.01) |
| *A61B 5/021* | (2006.01) |
| *A61B 5/02* | (2006.01) |
| *A61B 5/0456* | (2006.01) |

(52) U.S. Cl.
CPC ............ *A61B 8/04* (2013.01); *A61B 5/02007* (2013.01); *A61B 5/02116* (2013.01); *A61B 5/02125* (2013.01); *A61B 5/02014* (2013.01); *A61B 5/0456* (2013.01)

(58) Field of Classification Search
USPC .......................................................... 702/19
See application file for complete search history.

(56) References Cited

U.S. PATENT DOCUMENTS

| | | | |
|---|---|---|---|
| 4,475,554 | A | 10/1984 | Hyndman |
| 4,807,638 | A | 2/1989 | Sramek |
| 4,869,262 | A | 9/1989 | Orr et al. |
| 5,709,212 | A | 1/1998 | Sugo et al. |
| 5,730,146 | A | 3/1998 | Itil et al. |
| 5,876,353 | A | 3/1999 | Riff |
| 6,221,011 | B1 | 4/2001 | Bardy |
| 6,413,223 | B1 | 7/2002 | Yang |
| 7,179,228 | B2 | 2/2007 | Banet |

FOREIGN PATENT DOCUMENTS

| | | |
|---|---|---|
| EP | 0443267 A1 | 8/1991 |
| EP | 1150604 B1 | 8/2007 |

OTHER PUBLICATIONS

Teerlink et al., Serelaxin, recombinant human relaxin-2, for treatment of acute heart failure (RELAX-AHF): a randomized, placebo-controlled trial, www.thelancet.com vol. 381 Jan. 5, 2013 (29-39).
Teichman et al., Relaxin: Review of Biology and Potential Role in Treating Heart Failure, Curr Heart Fail Rep (2010) 7:75-82.
Dschietzig et al., Intravenous Recombinnt Human Relaxin in Compensated Heart Failure: A Safety, tolerability, and Pharmacodynamic Trial, Journal of Cardiac Failure vol. 15 No. 3 2009 (pp. 182-190).
Teerlink et al., Vasodilators in Acute Heart failure (AHF): Does Blood Pressure Matter?, Journal of Cardiac Failure Vor. 15 No. 6S-Suppl. 2009 (243).
Roytvarf et al., A Large-Scale, Energetic Model of Cardiovascular Homeostasis Predicts Dynamics of Arterial Pressure in Humans, IEEE Transactions on Biomedical Engineering, vol. 55, No. 2, Feb. 2008.
Lux et al., Limited Lead Selection for Estimation of Body Surface Potential Maps in Electrocardiography, IEEE Transactions on Biomedical Engineering, vol. BME-25, No. 3, May 1978 (pp. 270-276).

*Primary Examiner* — Jerry Lin

(57) ABSTRACT

Method and system for evaluating arterial pressure waves, vascular properties, as well as for diagnostic, physiological and pharmacological testing using various combinations of the following data acquisition and processing steps (some of the steps are optional): 1. Perturbing arterial pressure from its steady state. 2. Measuring the dynamics of at least one parameter related to the passage of arterial pressure waves along blood vessels. 3. Characterizing the magnitude and functional relation of changes in parameters described above in relation to changes in blood pressure during its displacement from and/or return to the steady state. 4. Classifying (comparing) the individual functional relation described above with a databank of parameters/functional relations for different states of vasomotor activity.

36 Claims, 10 Drawing Sheets

EVALUATING ARTERIAL PRESSURE, VASOMOTOR ACTIVITY AND THEIR RESPONSE TO DIAGNOSTIC TESTS

CROSS-REFERENCE TO RELATED APPLICATIONS

This application is a continuation-in-part of application Ser. No. 13/017,043, filed Jan. 30, 2011.

STATEMENT REGARDING FEDERALLY SPONSORED RESEARCH OR DEVELOPMENT

This invention was made with government support under the grant R43HL114277 awarded by the National Institutes of Health. The government has certain rights in the invention.

FIELD OF THE INVENTION

This invention relates to the field of biomedical methods and systems for evaluating and tracking arterial pressure, vascular activity, vascular elasticity, and autonomic nervous system activity, as well as methods and systems for diagnostic, physiological and pharmacological testing.

BACKGROUND OF THE INVENTION

Systemic arterial pressure regulation is vital for normal functioning of the brain and other internal organs in mammals. In a simplified form, the pressure is determined by the balance of forces between pumping force generated by the heart's muscle and mechanical resistance of arterial blood vessels. Thus, the pressure decreases when either the pumping force of the heart or arterial resistance decreases; it rises when the pumping activity of the heart or vascular resistance increase.

This large-scale, simplified concept of arterial pressure regulation has proved useful for pinpointing the primary factors responsible for abnormal pressure variations and designing therapies that target those factors to restore normal pressure. In particular, when arterial pressure exceeds normal limits and becomes too low or too high, a number of specific, "cardioactive" medications can be administered to increase or decrease pumping activity of the heart. On one side of the spectrum of cardioactive medications are beta-blockers and calcium blockers that diminish heart's activity and, therefore, decrease arterial pressure. On the other side are dobutamine and norepinephrine that produce an opposite effect. Another class of medications, referred to as the vasoactive medications, modifies the activity of smooth muscles in the vascular walls (vasomotor activity/tone, VMA), thus changing the size of the vascular lumen. Those medications include vascular smooth-muscle relaxants that increase vascular lumen, causing arterial pressure to decline, as well vascular smooth-muscle stimulants that decrease vascular lumen, increasing both vascular resistance and arterial pressure.

The relationship between arterial pressure and vascular properties described above can be also useful for clinical, physiological and pharmacological testing of new medications as well as designing new treatments for subjects with various cardiovascular disorders. Herein, the term subject denotes a living being, including human beings and animals. In particular, medications causing vascular relaxation have proved useful for treatment of patients with heart failure (HF) and dyspnea, who demonstrate a number of improvements in response to vasoactive medications, such as serelaxin (Teerlink et al.; RELAXin in Acute Heart Failure (RELAX-AHF) Investigators. Serelaxin, recombinant human relaxin-2, for treatment of acute heart failure (RE-LAX-AHF): a randomised, placebo-controlled trial. *Lancet* 2013; 381: 29-39.).

However, the overall effect of vasoactive medications in the studied patient populations has been modest or not statistically significant, suggesting that the magnitude of the responses to vasoactive substances varies from patient to patient and could be completely absent in some individuals. Indeed, Teerlink et. al. have shown that improvements in dyspnea are more likely to occur in the HF patients who have higher baseline arterial pressure (Teerlink et al. Vasodilators in Acute Heart Failure (AHF): Does Blood Pressure Matter? Results from Pre-Relax-AHF. Journal of Cardiac Failure 2009; 15:S74). This observation could have been expected, because higher arterial pressure is usually associated with higher peripheral (vascular) resistance, which is caused by greater VMA, as described above. Greater VMA, in turn, would result in more pronounced vasodilation in response to serelaxin or other vasorelaxants (or functional tests associated with vascular relaxation, e.g., exercise stress test) compared with subjects who have a low VMA. Thus, by examining baseline VMA, one can predict the magnitude of vasoactive response, identify subjects who would benefit the most from vasoactive medications and optimize (fine tune) dose/frequency of the drug intake for each subject.

SUMMARY OF THE INVENTION

This invention is a novel and non-obvious use of the method and system disclosed in the prior application Ser. No. 13/017,043, filed on Jan. 30, 2011, and incorporates herein by reference the disclosure contained in that application.

This invention describes a method and device (FIGS. 1 and 2) for the dynamical evaluation of arterial pressure dynamics, vascular properties, as well physiological effects of vasoactive substances and medications, using combinations of the following data acquisition and processing steps (combinations of processing steps can vary for different applications/settings):

I. Perturbation. Shifting arterial pressure and/or vascular smooth-muscle activity from its steady state is achieved using at least one physiological, psychophysiological or pharmacological maneuver (intervention or perturbation) selected from:
   A. Administration of a vasoactive medication, including alpha blockers (e.g., Phentolamine), vasorelaxants (e.g, serelaxin), vasopressors (e.g., epinephrine);
   B. Inflation and/or deflation of a pressurized cuff placed around a limb (e.g., arm, leg, wrist, fingers);
   C. Passive (without subject's active participation) or active (produced by the subject him/herself) changes in body position, including standing up, lying down, sitting down, etc.;
   D. Passive or active changes in the limbs' position (e.g., raising a leg or arm);
   E. Passive or active isometric muscular contraction (e.g., external muscular stimulation, active muscular contraction, such as Valsalva maneuver and other isometric muscular tests);
   F. Non-isometric muscular activity (e.g., physical exercises, walking, running, exercise stress-test);

G. Changes in breathing frequency, including faster or slower breathing, as well as temporary cessation of breathing activity and increased intra-thoracic pressure;

H. Psychological stress.

II. Monitoring cardiovascular signals. The monitoring includes multiple measurements or continuous registration of at least one signal related to the passage of arterial pressure waves along blood vessels over a selected period of time (the period of monitoring can be selected from a few seconds for a short-term test to minutes to hours to days for a longer term test). The period of monitoring includes: (i) a steady state (baseline) period before the intervention begins, (ii) the time of intervention, (iii) the period that immediately follows the intervention, and (iv) the period of return to the steady state. The monitored signals include an electrocardiogram and pulse-pressure (pressure-wave) signals. The following parameters are derived from the monitored signals and displayed in real time or analyzed after the recording is finished (off-line):

A. The time of occurrence of the R wave or some other ECG wave and/or fiducial point (e.g., P, Q, S, T or U wave). This time point in the cycle of cardiac electrical activity is used as an approximate estimate for the start time of the pressure wave generated by the contraction of the heart. We note that cardiac mechanical contraction has a time delay relative to the time of cardiac electrical activation on the ECG (approximately, 20-50 ms). However, this delay is relatively constant in all cardiac cycles, and therefore, can be factored out from the estimation of changes in pressure-wave velocity, as described below.

B. Pressure wave velocity (PWV) or pulse-wave velocity (FIG. 3), which is estimated as the ratio of the distance between two pressure-wave measurement points over the difference in pressure-wave arrival times between those two measurement points. (The difference in pressure-wave arrival times is commonly referred to as the pressure-pulse transit time or the pulse transit time, PTT.) As noted above, the time of the peak of the electrocardiographic R wave or some other time point on the ECG signal can be also used as one of the measurement time points (as an approximate start time of the pressure wave being generated by heart's contraction);

C. Pressure wave amplitude (FIG. 3), including its $1^{st}$, $2^{nd}$ and $3^{rd}$ peak, the area of the pressure wave and the areas of its $1^{st}$, $2^{nd}$ and $3^{rd}$ peak; the $1^{st}$ and $2^{nd}$ derivatives of the pressure wave;

D. The augmentation index (AI), defined as the ratio of an absolute difference in the amplitude of the $1^{st}$ and $2^{nd}$ pressure peaks ($PA_1$ and $PA_2$, respectively) over the total amplitude of the pressure wave (PA):

$$AI = \frac{|PA_1 - PA_2|}{PA} \quad (1)$$

E. The time duration of the $1^{st}$, $2^{nd}$ and $3^{rd}$ peaks of the pressure waves and of the entire pressure wave (FIG. 3).

F. The time intervals between the $1^{st}$, $2^{nd}$ and $3^{rd}$ peaks of the pressure waves (FIG. 3).

G. The systolic, diastolic, mean arterial pressure, as well as the median, mode, standard deviation, variance and range of temporal (i.e., between serial measurements performed at the same sensor locations) and spatial (i.e., between different sensor locations) variation of the systolic, diastolic and mean arterial pressure.

Although the method of the present invention can be implemented using a single monitored parameter (e.g., PTT), it preferably, includes simultaneous monitoring of at least two or more parameters.

III. Preprocessing (optional) includes:

Filtering (optional) of the power-line interference, ambient noises, artifacts and electromagnetic interference, random noise, low-frequency variations introduced by breathing and other physiological and non-physiological noise. The filtering can be achieved using fixed or adaptive filters implemented in electronic circuitry (hardware implementation), firmware or software (software implementation). The filtering can be also performed using:

a. pattern recognition or an orthogonal linear decomposition, which includes determining the characteristic (typical) basis vectors or eigenvectors and associated eigenvalues and constructing a typical template using a linear combination of basis vectors associated with the greatest eigenvalues;

b. wavelets, which provide an optimized windowing function for the filtering; or c. other signal processing methods.

Signal calibration (optional), which includes renormalization of the signal according to a reference signal or values. This may include dividing fiducial points or segments of the reference signal by the corresponding points or segments of the calibrated signal to determine the calibration coefficients. For example, dividing the total magnitude (range) of a local pressure waveform by the range of systemic pressure values (i.e., systolic pressure-diastolic pressure) determined in mm Hg yields a calibration coefficient that can be used to derive arterial pressure range from local pressure wave measurements (multiplying those measurements by the calibration coefficients).

Signal calibration may also include determination of the functional relationship between two or more reference points in a reference signal or in two or more reference signals (e.g., systolic pressure, diastolic pressure, mean pressure, pressure wave's amplitude, area, up-slope and down-slope, curvature, amplitude and duration of $1^{st}$, $2^{nd}$ and $3^{rd}$ peak, AI index). In this case, calibration (renormalization) formula may include a time segment of data (instead of a single time point) or a combination of points (segments) in several signals obtained by several sensors (e.g., pressure waves registered by several accelerometers, as shown in FIG. 8-10).

IV. Processing includes determining (characterizing) the patterns of functional relationships between monitored signals and/or parameters described above (section 2. Data monitoring). Specifically, the patterns of functional relations can be characterized in terms of:

a. statistical indicators, parameters and/or estimators, including mean, median, mode, range, variance and standard deviation;

b. spectral indicators/estimators (e.g., total power and/or energy of the signal, magnitude and phase of spectral energy in specific frequency bands);

c. functional relationships, including:

i. linear relationships, which are characterized by slope and axis intercept points.

ii. nonlinear relationships, which are characterized by the steepness (slope) and location of linear regions, concavity (up or down) or, alternatively, the $1^{st}$ and $2^{nd}$ derivatives. For example, the relationship between mean pressure and pressure wave velocity during a relaxed state of vascular activity (after physical exercises) has a nonlinear, concave-down shape. However, this relationship becomes inverted (concave-up), during Valsalva maneuver, which is associated with contraction of vascular smooth muscles. Averaging of these two inverse-type relationships, produced an averaged, linear function (Roytvarf A., Shusterman V. A Large-Scale, Energetic Model of Cardiovascular Homeostasis Predicts Dynamics of Arterial Pressure in Humans. IEEE Transactions on Biomedical Engineering 2008, 55: 407-418). Theoretically predicted, qualitative pattern of relationships between diastolic blood pressure and pressure wave velocity for relaxed and contracted states of vascular activity are shown in FIG. 2. The figure shows that the state of vascular activity determines not only the steepness but also the curvature of the relationship between key cardiovascular parameters. These nonlinear properties must be taken into account for accurate characterization of cardiovascular responses to physiological, psychological and pharmacological tests.

iii. correlation and coherence between the studied parameters, including changes in vascular activity, systolic, diastolic and mean pressure.

d. space-time maps (distributions) of at least one parameter selected from pressure wave isochrones (isochronal maps), amplitudes (isoamplitude maps), areas (isoarea maps), isochrones' derivatives, amplitudes' derivatives, local pressure-wave's peaks, durations of local pressure-wave's peaks, time intervals between local pressure-wave's peaks, as well as combined distributions of two or more pressure-wave parameters listed above (i.e., higher-dimensional maps).

V. Classifying (optional) includes comparing an individual's functional relationships described in #4 above with a databank of parameters/functional relations for different states of vasomotor activity, using at least one measure of similarity and/or difference(s) between an individual's and typical parameter values and/or patterns of such relationships. There are two types of typical parameter values and patterns of functional relationships: (i) an individual's typical parameters/patterns and (ii) group based typical parameters/patterns. The first type is based on an individual's historical (baseline, serial) data and is determined using the methods of time-series analysis, pattern recognition, artificial intelligence and other analytical tools. The second type is group (population) based typical parameters/patterns of functional relationships; it is determined from the group data using statistical approaches, pattern recognition, artificial intelligence and other methods. Both types of parameters/patterns, as well as methods for determining them, have been disclosed in the prior-art U.S. Pat. Nos. 7,485,095, 7,801,591 and 8,388,530 to Shusterman.

Measures of similarity may include cross-correlation and cross-coherence, distance measurements (Eucledian, Mahalonobis distances), cluster analysis, and other measurements, which can be combined with discriminant analysis, renormalization techniques, pattern recognition, methods of artificial intelligence and other statistical estimators.

System Sensors and Data Acquisition Hardware.

This invention makes use of the technologies for tracking pressure waves in the arteries/blood vessels (herein referred to as the pressure-wave sensors). The pressure waves can be detected using a number of currently available sensors, including photoplethysmographic sensors, impedance-plethysmography (plethysmographic) sensors (which measure changes in the electrical impedance/resistance in the chest cavity associated with the heart's contractions and resulting redistribution of blood fluid), accelerometer and/or microelectromechanical (MEMS) sensors attached to the skin surface in vicinity of blood vessels, as disclosed in Shusterman's pending patent application Ser. No. 13/017,043, as well as ultrasound sensors and volume-clamp technologies, which utilize pressurizing cuffs on the extremities (e.g., the pressurizing cuffs used in Finometer manufactured by Finapres Medical Systems, Amsterdam, Netherlands), as well as a combination of ECG and other pressure-wave sensors, as described below.

Monitoring the pressure waves using multiple accelerometer (MEMS) sensors placed in vicinity of multiple blood vessels or in different segments of the same vessel, as disclosed in Shusterman's application Ser. No. 13/017,043, opens the possibilities for improved tracking of both systemic changes in vascular activity and local changes in different vessels. In addition, the multiple sensors enable the tracking of changes in pressure wave velocity (or its inverse function, the pulse-transit time), by calculating the time difference between the arrival of the pressure waves at different sensors' locations. Alternatively, the pressure wave velocity can be calculated as the time difference between the R-peak (or other peaks) of the ECG signals and the times of arrival of the pressure waves at the locations of the sensors placed in vicinity of blood vessels (arteries). The advantages of using ECG signals include relatively simple and convenient data acquisition, relatively high signal-to-noise ratio and robustness to movement artifacts. An additional advantage is that ECG peaks can be measured from a number of different locations on the surface of the body; the times of occurrence of the ECG peaks would be essentially the same. For example, the time of occurrence of the biggest ECG peak would be the same for the measurements performed by two sensors positioned as follows: (i) on the left and right wrist, (ii) in the left and right subclavian regions, (iii) on the left and right sides of the neck, (iv) on the left and right sides of the head, (v) on the right arm and left leg, (vi) on the left arm and left leg, (vii) on the right arm and precordial region (between the sternum and left midaxillary line).

In some settings, it is convenient to combine at least some of the sensors used in the system of the present invention, as described above, within a single enclosure or "patch sensor" (FIG. 11). Examples of such patch sensors include: (i) two electrocardiographic sensors and a sensor adapted for registering mechanical movements of the body, particularly, passage of the pressure waves (e.g., an accelerometer, MEMS sensor, photoplethysmographic sensor, impedance-plethysmography sensor, voltage-clamp sensor, ultrasound sensor, etc.)

The method of the present invention can be practiced in both laboratory and real-life setting. In the real-life setting, perturbations of arterial pressure are provided by environmental and behavioral factors (e.g., physical exercise, psychological stress, work-related stress, etc.)

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
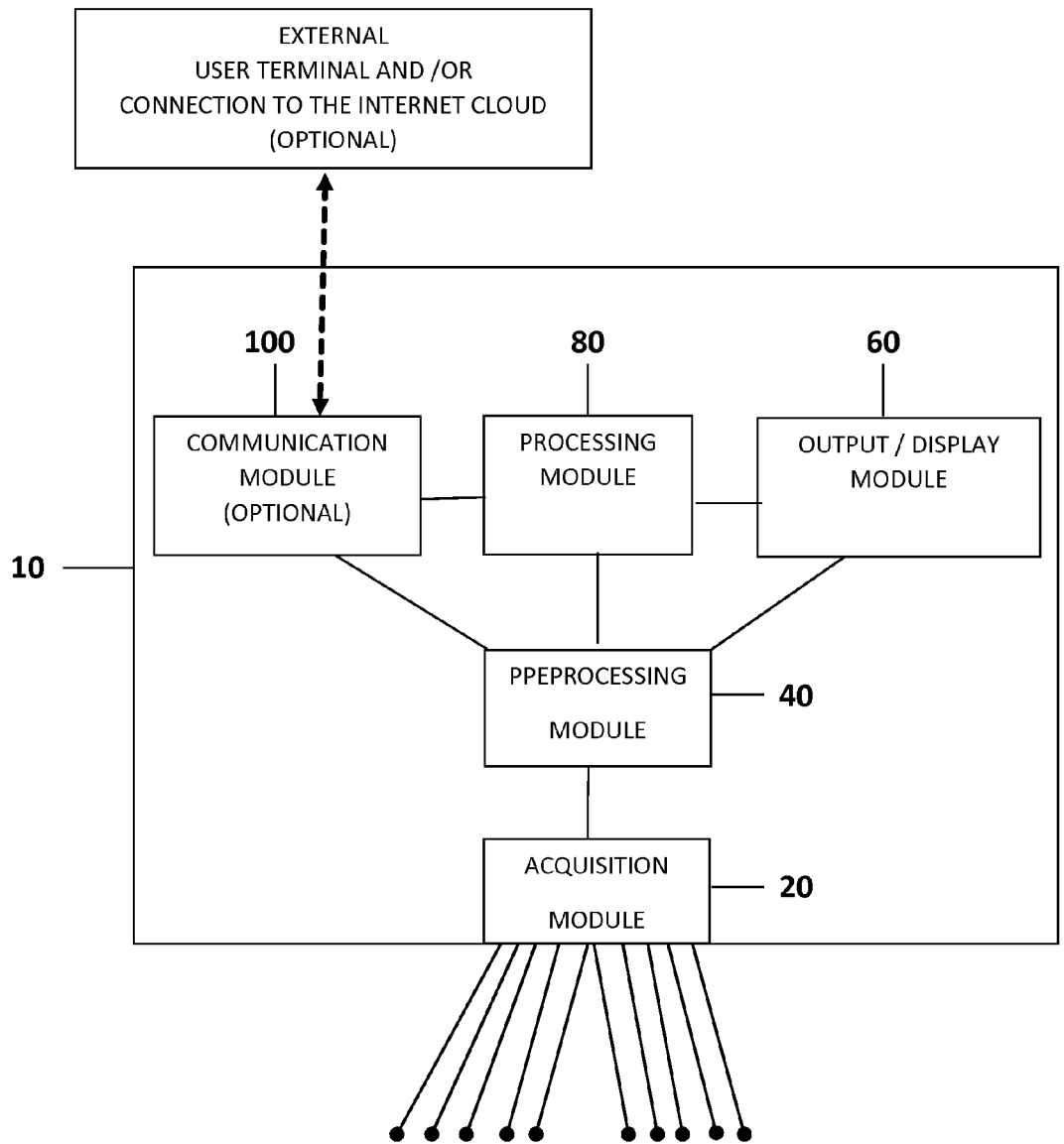
FIG. 1 is a block-diagram of a preferred embodiment of the system architecture.

FIG. 1 is a block-diagram of a preferred embodiment of a device 10 of this invention. The device includes:
a. an acquisition module 20 (Note that the words "module" and "unit" are used interchangeably and have the same meaning throughout this document),
b. a preprocessing module 40,
c. an output/display module 60,
d. a processing module 80,
e. an optional communication unit 100, and
f. an optional external user terminal and/or connection to the Internet cloud.

The acquisition module 20 is connected to sensors for measuring at least one signal generated or associated with the passage of arterial pressure waves along the vascular tree. The number of sensors and their type are selected according to the specific requirements of a particular application. For example, Shusterman's application Ser. No. 13/017,043 discloses accelerometer sensors and/or other microelectromechanical systems, which can be positioned in multiple locations along major blood vessels. Other sensors, including sound (microphones), ultrasound, infrared, radio-frequency, electromagnetic, electrical impedance and other sensors, can be used for tracking arterial pressure waves.

Figure 3:
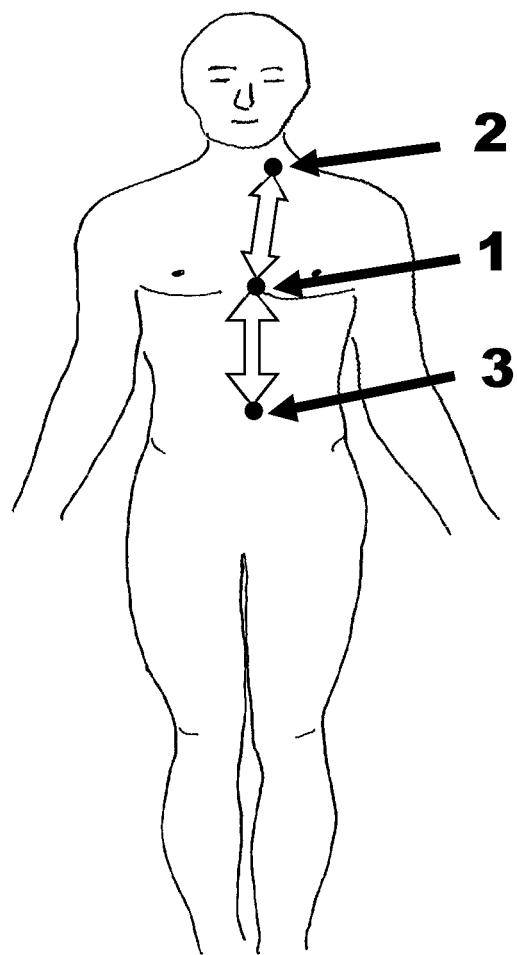
FIG. 3 is an example of sensor locations used for tracking pressure waves in pilot experiments with a system prototype.
Figure 9:
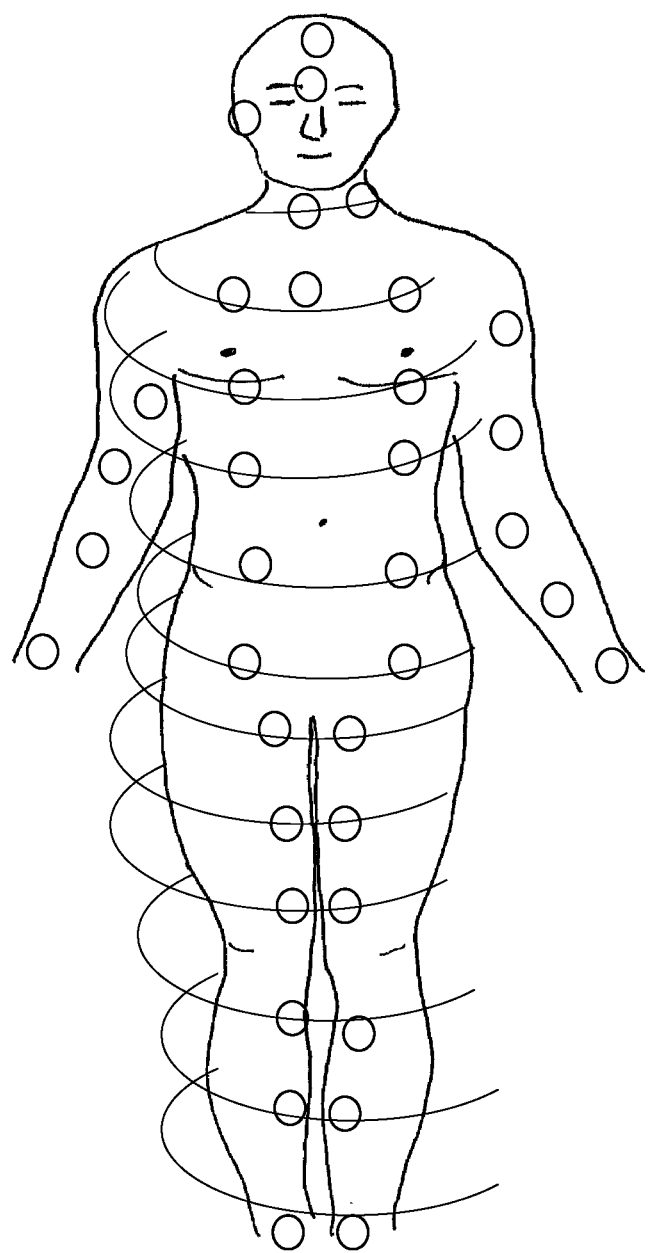
FIG. 9 is another example of sensor locations for tracking pressure waves, showing theoretically predicted (spatially "regular") distribution of pressure-wave arrival times (isochrones, isochronal map) at different locations in a normal arterial system.
Figure 10:
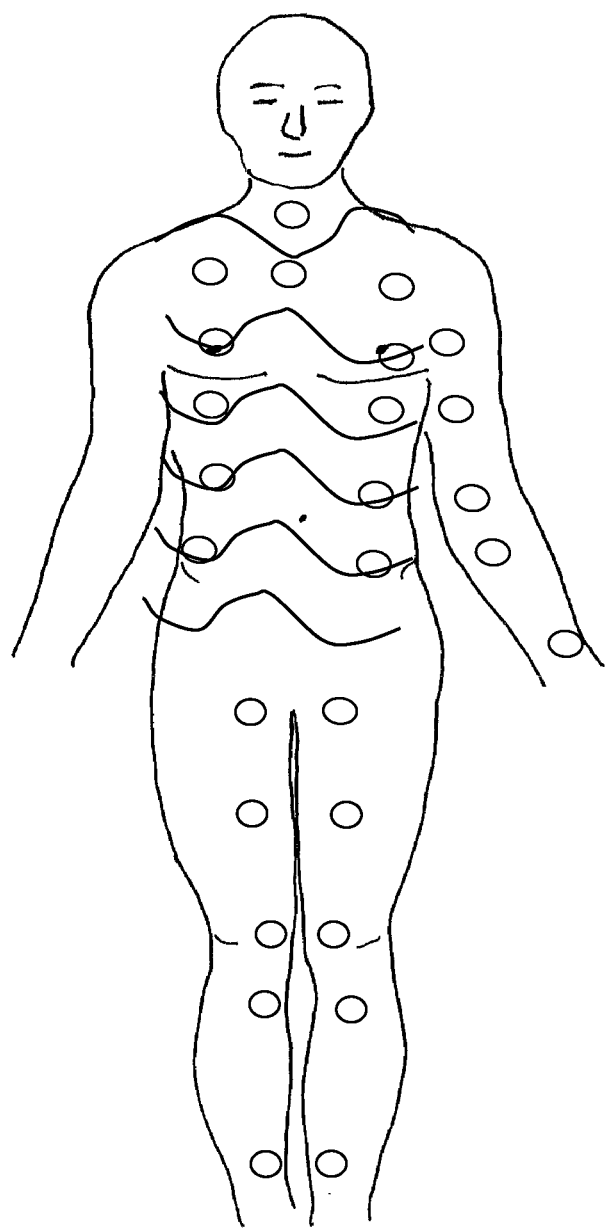
FIG. 10 shows theoretically predicted (spatially "irregular") distribution of pressure-wave arrival times in an abnormal arterial system (e.g., aneurisms, non-uniform atherosclerosis of the vascular walls).

In a simple, cost- and size-minimized configuration, module 20 has only one sensor for detecting the passage of arterial pressure wave and two or three ECG electrodes, which are used for detecting the peak of the R wave or some other fiducial point in the ECG signal (FIG. 3). The fiducial point in the ECG signal provides approximate start time of the pressure wave generated by the heart contraction, as described above. In such a minimized configuration, module 20 contains ECG electrodes and sensor for detecting arterial pressure waves within a single, miniaturized unit. This miniaturized configuration is useful as a screening and first-response tool for paramedics, emergency medical personnel as well as a personal checkup tool for individuals at home or on the road. An alternative minimized configuration uses two pressure-wave sensors (i.e., in configuration, the $2^{nd}$ pressure-wave sensor/signal replaces the ECG sensors/signal). By contrast, multiple sensors are required for the mapping of spatial distribution of the pressure waves, as shown in FIG. 8-10, and other applications.

Preprocessing module 40 filters the signals from noise and electromagnetic interference, which are unavoidable in both real-life and laboratory settings. The filtering can be implemented in the electronic circuitry (hardware implementation) and software/firmware (software implementation) and may include fixed filters, finite-impulse response (FIR), infinite impulse response (IIR), wavelets, Kalman filter and adaptive filters. The preprocessing may also use pattern recognition techniques to separate signal from noise. Power-line interference represents a well-known problem and can be minimized using common-mode rejection implemented in the electronic circuitry or software.

Output/display unit displays the waveforms and/or filtered signals obtained from Preprocessing module 40, as well as results of processing and analysis (e.g., changes in arterial pressure, vasomotor activity, baroreflex, vascular elasticity) obtained from Processing module 80.

Figure 6:
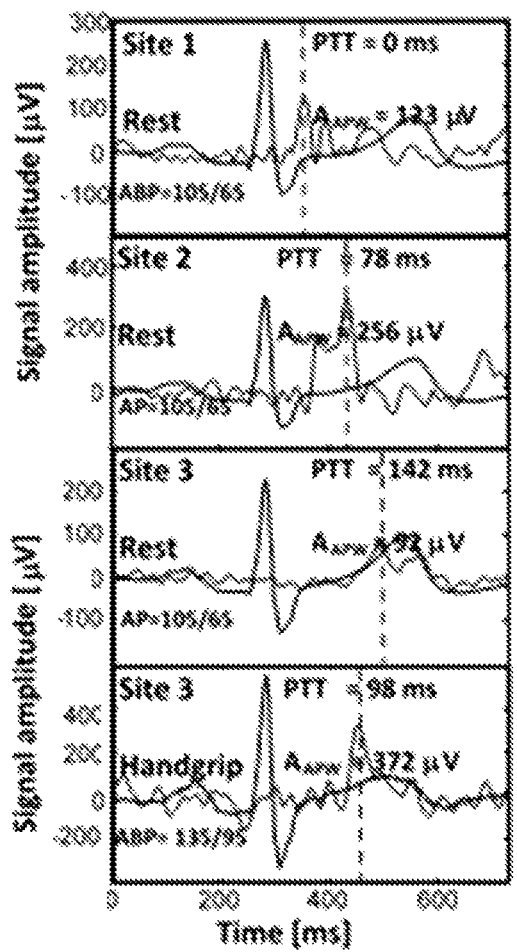
FIG. 6 shows changes in pulse-transit time (PTT), arterial pressure and pressure-wave amplitudes registered at Sites 1, 2 and 3 in FIG. 3.
Figure 7:
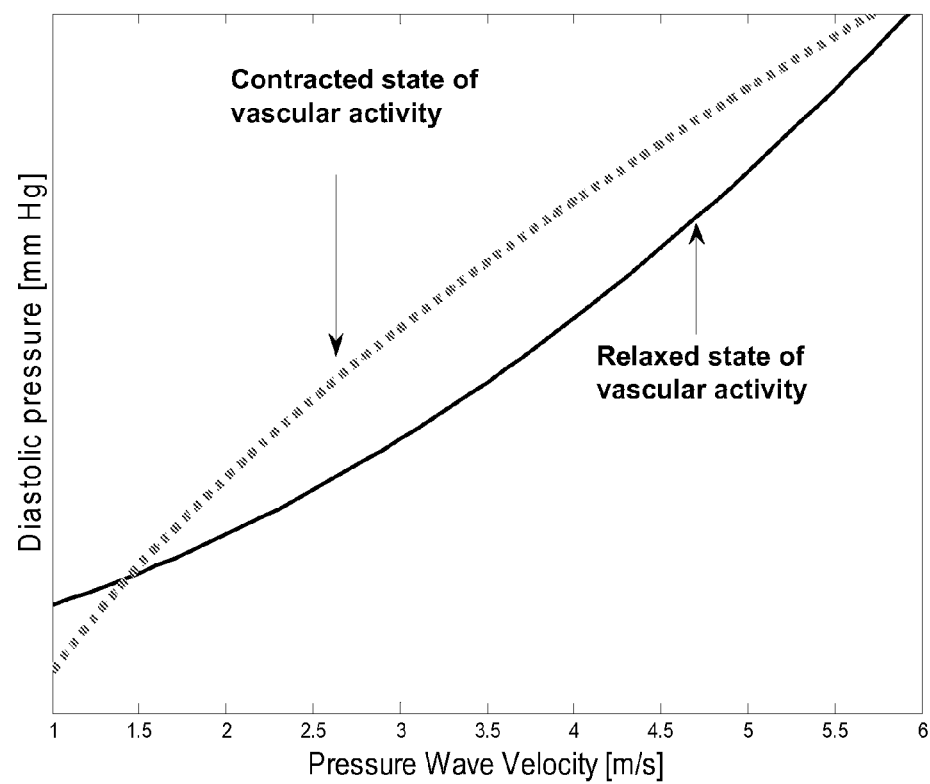
FIG. 7 is a graph of qualitative relationship between diastolic arterial pressure and pulse wave velocity, which has been predicted theoretically.
Figure 8:
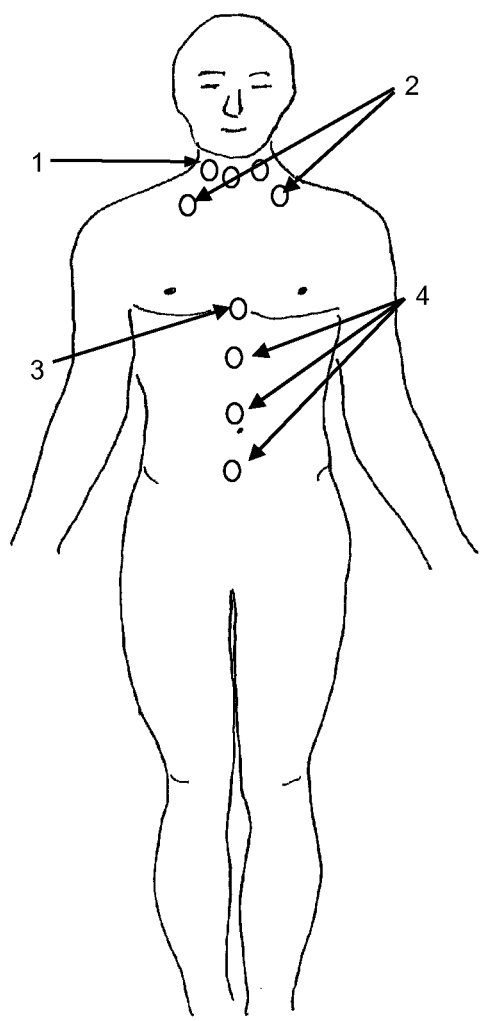
FIG. 8 is an example of sensor locations along major arteries for tracking pressure waves.

Processing module 80 receives filtered signals from the Preprocessing module 40 and performs at least some of the following processing and classification steps (the specific combination of steps depends on specifics of a particular application):
a. extracts from the signals monitored parameters, including the time of the fiducial points (e.g., the peak of the ECG R wave, the beginning, peak and end of the pressure wave, the $1^{st}$, $2^{nd}$ and $3^{rd}$ peaks of the pressure waves), using amplitude and/or derivative thresholds, feature extraction, wavelets, waveform analysis, pattern recognition (e.g., an orthogonal linear decomposition and identification of the basis vectors or eigenvectors which are arranged in the order of their respective eigenvalues, so that the vectors corresponding to the greatest eigenvalues represent the most typical features of the pattern and are utilized as a template for feature extraction and/or detection of the waveform patterns) and comparison with diagnostic criteria (thresholds);
b. calibrates monitored signals and/or parameters using an individual's baseline values, as described above;
c. determines characteristics of the response to intervention described above, including the magnitude, range, speed (time length), pattern of temporal changes (e.g., linear, concave up or down), and pattern of spatial changes, as shown in FIG. 6-8; and
d. classifies an individual's pattern of response to perturbation by assessing similarity and/or differences with those for the same or similar group/population of subjects.

An optional Communication unit 100 allows data transmission to an external user terminal (e.g., personal computer, computer tablet, smart phone) and/or Internet cloud. The transmission can be wireless (using RF-communication, such as Bluetooth, Wi-Fi, Zigbee, cell-phone, etc.) or wire (cable) connection. The external user terminal on a PC, laptop, smart phone, tablet PC or Internet cloud can be used for data display, further analysis, editing, archiving, printing and other functions.

Figure 2:
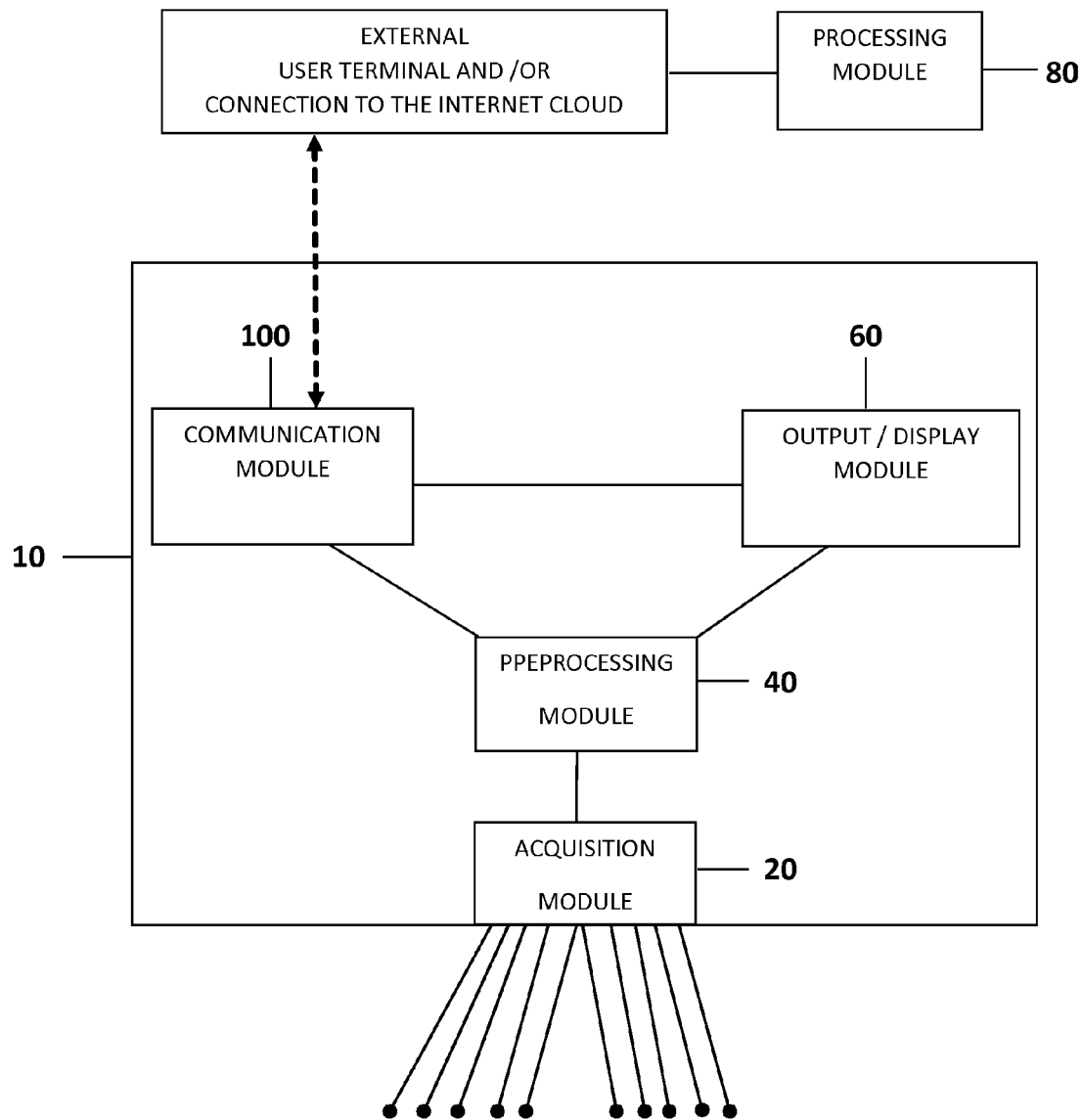
FIG. 2 is a block-diagram of another embodiment of the system architecture.

FIG. 2 is a block-diagram of another embodiment of a device 10 of this invention. The main difference with the preferred embodiment shown in FIG. 1 is in the external location of the Processing module 80. This configuration minimizes the size and cost of the device 10 and is appropriate for networked devices and some applications where on-site, real-time data tracking is not essential. For example, such configuration can be used in the devices, which provide tracking of patients' data and transmit those data to a central monitoring station using a wireless or wire-based communication. The central monitoring station can be located at a medical center or on an Internet cloud (a virtual medical center).

FIG. 3 shows examples of sensor locations used for pilot experiments of system prototype of this invention, which includes sensors for measuring electrocardiogram (ECG) and 3-axial accelerometer (MEMS) sensors. The accelerometer sensors are positioned along the main arteries (aorta) to register the mechanical displacements, which arise at the time of the pressure wave arrival near the sensors' locations. As described above, the ECG sensors are used for determining approximate start time of the pressure wave in the left ventricle by measuring a fiducial point of the ECG waveforms (e.g., the peak of the R wave).

Figure 4:
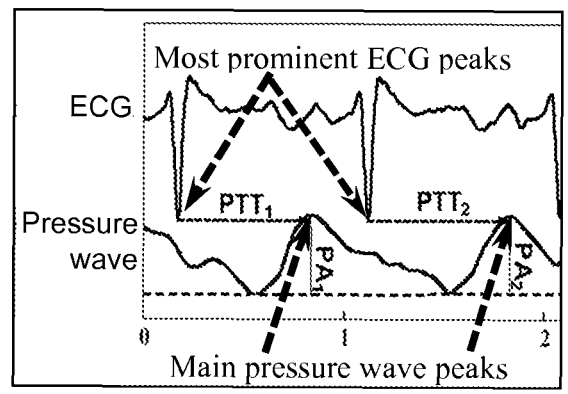
FIG. 4 shows simultaneous measurement of ECG and pressure-wave signals, detection of peaks in ECG and pressure wave signals, as well as measurement of the pressure wave amplitude (PA) and pulse-transit time (PTT) using the two signals.
Figure 5:
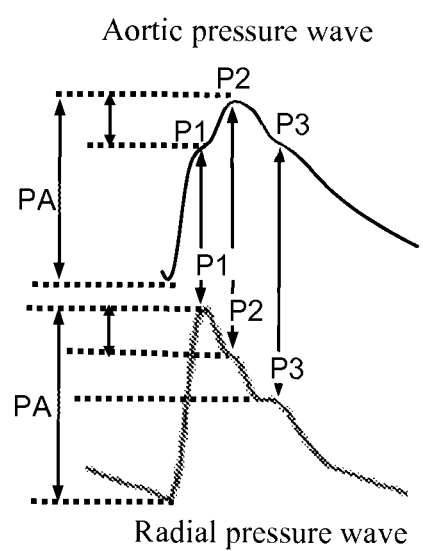
FIG. 5 shows pressure wave patterns in the aorta and radial artery, as well as amplitudes and local peaks of the pressure waves.

FIGS. 4 and 5 show signals recorded by the ECG and pressure-wave sensors located in the vicinity of the aorta and radial artery, as well as the parameters extracted from those signals, including:
  A. The (arterial-pressure) pulse transit time (PTT), which is determined as the time interval between the most prominent ECG peak and the peak of the passing pressure wave, which is detected by the accelerometer sensor when the pressure wave in the aorta reaches the sensor location;
  B. Pressure wave amplitude (PA) measured as the amplitude difference between the maximum and minimum of the pressure wave;
  C. Amplitudes, areas, $1^{st}$ and $2^{nd}$ derivatives of the $1^{st}$, $2^{nd}$ and $3^{rd}$ peaks of the pressure wave ($P_1$, $P_2$, $P_3$), which are produced by the reflections of the pressure waves in various parts of the arterial tree;
  D. Time lengths and time intervals between the $1^{st}$, $2^{nd}$ and $3^{rd}$ peaks of the pressure wave ($P_1$, $P_2$, $P_3$)
  E. The augmentation index determined as the ratio of an absolute difference in the amplitude of the $1^{st}$ and $2^{nd}$ pressure peaks ($PA_1$ and $PA_2$, respectively) over the total amplitude of the pressure wave (PA), as shown in formula (1).

FIG. 6 shows examples of ECG and pressure waveforms (which are superimposed over each other) recorded using the prototype system and sensor locations shown in FIG. 3.ABdividing the distance traveled by the pressure wave (e.g., from the left ventricle to accelerometer's location) by PTT yields the pressure wave velocity (PWV). This speed is directly proportional to arterial pressure, because the pressure wave travels faster when the pressure increases. However, PWV is also affected by vascular stiffness; it increases when arterial walls become stiffer (less elastic). As disclosed in Shusterman application Ser. No. 13/017,043, the changes in arterial stiffness are highly variable in peripheral arteries (e.g., in the finger arteries), and this variability represents a major obstacle in the derivation of arterial pressure using the measurements obtained from peripheral arteries. However, as further disclosed in Shusterman application Ser. No. 13/017,043, the arterial stiffness is essentially unchanged (constant) in the aorta and large vessels, which allows one to derive and track changes in arterial pressure from pressure-wave's amplitude and PTT measurements obtained in the large vessels. As FIG. 6 demonstrates, PTT becomes shorter (i.e., pressure wave velocity increases), when systemic arterial pressure increases due to handgrip compared to rest (105/65 to 135/95 mm Hg), PTT measured between the peak of the R wave in the ECG and the peak of the pressure wave in the abdominal aorta, as measured by an accelerometer positioned at Site 3 in FIG. 3.

FIG. 7 shows theoretically predicted shapes of relationships between the PWV and diastolic pressure for different states of vascular activity, which are elicited by different types of interventions in healthy volunteers (Roytvarf A., Shusterman V. A Large-Scale, Energetic Model of Cardiovascular Homeostasis Predicts Dynamics of Arterial Pressure in Humans. IEEE Transactions on Biomedical Engineering 2008, 55: 407-418). The relaxed state of vascular activity is elicited by aerobic exercise (e.g., on a bicycle or treadmill), whereas the contracted state of vascular activity is elicited by an isometric muscle contraction during Valsalva maneuver. In particular, the experimental and theoretical study by Roytvarf and Shusterman cited above showed that a qualitatively similar relationship (to that shown in FIG. 6) exists between PWV and mean arterial pressure (MP), which is calculated as:

$$MP=(SP+2 \cdot DP)/3 \qquad (2)$$

where SP is the systolic pressure and DP is the diastolic pressure. Thus, the weight of diastolic pressure is two-fold greater than that of systolic pressure, which suggests that the shapes of the relationships between PWV and MP is similar to those for PWV and DP. These theoretical predictions are shown in FIG. 6.

FIG. 8 shows the following locations or sites (which are marked by circles) for tracking passage of the pressure waves in central arteries/blood vessels (aorta, carotid arteries and subclavian arteries):
  Site 1: Neck: center, left and right carotids.
  Site 2: Subclavian arteries, left and right.
  Site 3: Descending aorta, left-subxiphoid region.
  Site 4: Abdominal aorta: upper, umbilical and lower abdominal regions.

Other possible sensor locations include ascending aorta, thoracic aorta, pulmonary artery, renal arteries, carotid arteries, subclavian arteries, radial arteries, digital arteries, dorsalis pedis artery and its branches. The sensor locations can be changed and optimized according to setting and application specifics, age, gender, medical history diagnosis, blood vessels, or region of vascular tree being investigated.

FIG. 9 shows theoretically predicted spatial distribution of the pressure wave characteristics (e.g., pressure-wave arrival times, amplitudes, $1^{st}$, $2^{nd}$ and $3^{rd}$ peak amplitude and durations) in major arteries in a healthy individual. The distribution has a regular, uniform shape, showing that all vascular walls have similar wall composition (elasticity) and that there are no major non-uniformities in the diameter of blood vessel (e.g., caused by aneurisms or atherosclerosis).

FIG. 10 shows theoretically predicted spatial distribution of the pressure waves in major arteries in a person with vascular abnormalities, which in contrast to those shown in FIG. 8, lead to a non-uniform, irregular distribution pattern of pressure wave characteristics e.g., pressure-wave arrival times, amplitudes, $1^{st}$, $2^{nd}$ and $3^{rd}$ peak amplitude and durations). Such non-uniform distributions are predicted for blood vessels abnormalities, which can be due to aneurisms or atherosclerosis.

Figure 11:
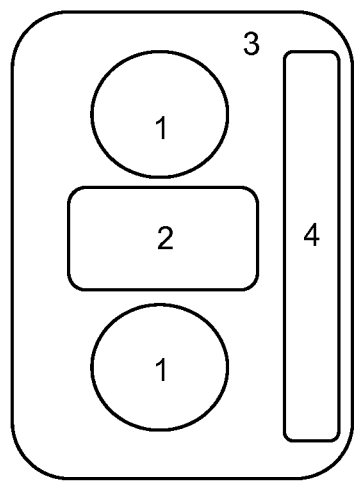
FIG. 11 shows an example of a patch sensor, which incorporates: (i) two electrocardiographic sensors and a sensor adapted for registering mechanical movements of the body, particularly, passage of the pressure waves (e.g., an accelerometer, MEMS sensor, photoplethysmographic sensor, impedance-plethysmography sensor, voltage-clamp sensor, ultrasound sensor, etc.)

FIG. 11 shows an example of a patch sensor, which incorporates two electrocardiographic sensors 1 and a sensor adapted for registering mechanical movements of the body, particularly, passage of the pressure waves 2 (e.g., an accelerometer, MEMS sensor, photoplethysmographic sensor, impedance-plethysmography sensor, voltage-clamp sensor, ultrasound sensor, etc.). The sensors are embedded within the patch material 3, which is covered by an adhesive substance to provide good attachment to the skin surface. The patch may also contain a communication module 4 (e.g., Bluetooth, ZigBee, Wi-Fi, etc.), or it can be attached to an external communication module by a cable, directly or via the cable connector.

Example 1. Testing the Effectiveness of Vasoactive Medications

The following hypothetical example illustrates application of the present invention for testing the efficacy of a vasoactive medication (serelaxin) for managing acute heart failure. Similarly, the present invention can be applied for testing other vasoactive medications and in other patient populations.

Serelaxin, recombinant human relaxin-2, is a vasoactive hormone that produces multiple hemodynamic effects primarily associated with vasodilation. In patients with acute heart failure (AHF), it increases arterial compliance, cardiac output, and renal blood flow, reduces dyspnea, and moderately decreases systemic arterial and pulmonary wedge pressures (Teerlink et al.; RELAXin in Acute Heart Failure (RELAX-AHF) Investigators. Serelaxin, recombinant human relaxin-2, for treatment of acute heart failure (RELAX-AHF): a randomised, placebo-controlled trial. *Lancet* 2013; 381: 29-39. Dschietzig et al. Intravenous recombinant human relaxin in compensated heart failure: a safety, tolerability, and pharmacodynamic trial. *J Card Fail.* 2009:182-90. Teichman et al. Relaxin: review of biology and potential role in treating heart failure. *Curr Heart Fail Rep* 2010; 7: 75-82.) However, the magnitude of relaxin-evoked effects varies from patient to patient and is difficult to forecast in each particular case. It has been shown, for example, that improvements in dyspnea are more likely to occur in patients who have higher baseline arterial pressure. (Teerlink et al. Vasodilators in Acute Heart Failure (AHF): Does Blood Pressure Matter? Results from Pre-Relax-AHF. *Journal of Cardiac Failure* 2009; 15:S74) Mechanistically, this effect is most likely determined by individual differences in baseline smooth-muscle tone (SMT), so that more pronounced relaxin-induced vasodilation occurs in subjects with greater baseline SMT, which is usually associated with higher arterial pressure. Thus, by examining baseline SMT, it is possible to identify AHF patients who would benefit the most from this medication and optimize the dose for each subject.

In this hypothetical example, a 50-year old patient with AHF has been given the test of the present invention to determine baseline vasomotor activity and the magnitude of the response to serelaxin, as manifested by changes in the pressure wave characteristics described in the summary of the invention. The test has shown that none of the pressure wave characteristics, including pressure wave amplitude, its area, $1^{st}$ and $2^{nd}$ derivative, pulse wave velocity, magnitude and duration of the $1^{st}$, $2^{nd}$, and $3^{rd}$ peaks of the pressure waves has changed after the medication. Given this minimal response, administration of serelaxin has been stopped.

Example 2. Detection and Localization of Vascular Abnormalities Using Spatio-Temporal Distribution of Pressure Waves in Major Arteries This hypothetical example shows application of the present invention for the detection and localization of vascular abnormalities, including atherosclerotic plagues and aneurisms. A screening procedure is conducted in a hypothetical, 60-year old subject with arterial hypertension and arterosclerosis, using multiple accelerometers attached in vicinity of major arteries around the torso (including the chest, abdomen and back), as well as the neck, head and extremities, as shown in FIGS. 8 and 9. After the initial intervention administered using an exercise stress test, the recovery of the pressure-wave characteristics described above would show any local heterogeneity (irregularity) detected by accelerometers positioned in the region of abdominal aorta. Subsequent ultrasound tests would reveal an aortic aneurism.

Example 3. Differentiating Atherosclerotic Loss of Vascular Elasticity from the Contractile State of the Smooth Muscle Activity in Arterial Walls Differentiating permanent changes in vascular elasticity due to atherosclerosis from those caused by increased smooth muscle activity is challenging. This hypothetical examples illustrates application of present invention for those purposes.

In a hypothetical, 50-year old man with arterial hypertension, an initial intervention (exercise stress test) produced a 10% change in the pulse wave velocity compared with the average changes observed in the same age and sex group. A second intervention (Valsalva maneuver) also resulted in 15% change in those parameters compared with age/sex adjusted average values. The typical curved patterns of the relationships between the PWV and diastolic pressure were "flattened" (i.e., the curvatures were largely absent). This led to a conclusion of pronounced atherosclerotic changes of large arteries (as opposed to the possibility of increased vascular smooth-muscle tone).

Example 4. Diagnosis the State of Vascular Autonomic Nervous System Activity

The vascular activity is controlled by the sympathetic nervous system. It is important to evaluate the magnitude of the sympathetic modulation in patients with hypertension, heart failure, ischemic and non-ischemic cardiomyopathies, and other cardiovascular disorders.

In this hypothetical example, a 30 year old female underwent initial interventions (exercise test and Valsalva maneuver), and her PWV/diastolic pressure relationship showed a 50% greater curvature and magnitude of changed compared with age and sex-adjusted mean values. This led to the conclusion of increased sympathetic modulation and administration of sympatholytic medications.

Example 5. Predicting and Tracking the Effectiveness of Vasoactive Medications in Patients with Hypertension Arterial hypertension is a significant public health problem, which afflicts 40 million Americans. Although a number of medications are used for treatment of high blood pressure, finding an optimal combination of drugs, dosage and frequency is challenging. This hypothetical example illustrates application of the present invention for the assessment of the efficiency of vasoactive medications in subjects with hypertension.

In a 40-year old female with arterial hypertension, an initial intervention (exercise stress test) was inclusive. A subsequent exercise and intake of vasorelaxants showed a significant decrease in diastolic pressure compared with the $1^{st}$ test. This confirmed the efficiency of vasorelaxants for controlling blood pressure in this individual.

Nothing in the above and attached descriptions is meant to limit the present invention to any specific materials, geometry, or orientation of elements. Many modifications are contemplated within the scope of the present invention and will be apparent to those skilled in the art. The embodiments disclosed herein were presented by way of example only and should not be used to limit the scope of the invention.

Whereas particular aspects of the method of the present invention and particular embodiments of the invention have been described for purposes of illustration, it will be appreciated by those skilled in the art that numerous variations of the details may be made without departing from the invention as described in the appended claims.

What is claimed is:

1. A method for dynamical evaluation of at least one indicator selected from arterial pressure, cardiac output, and vascular properties, said method comprising:
    placing at least two sensors, at least one of which contains an accelerometer adapted for placement on the surface of an individual's torso and is adapted for registering at least one torso-surface movement related to cardiovascular mechanical activity,
    collecting data from said at least two sensors over multiple cardiac cycles; and
    processing said data, wherein said processing is adapted to determine at least two parameters of cardiovascular activity and is further adapted to derive at least one parameter of cardiovascular mechanical activity related to the arterial pressure in the central arteries.

2. A method as set forth in claim 1 that includes preprocessing said physiological signals to separate said signals from noise and interference using at least one method selected from filtering using fixed filters, filtering using adaptive filters, pattern recognition, orthogonal linear decomposition, and wavelet decomposition.

3. A method as set forth in claim 1 in which said processing further includes calibrating said parameters with respect to at least one reference value selected from:
    i. systolic pressure;
    ii. diastolic pressure;
    iii. mean arterial pressure;
    iv. hear rate;
    v. vascular properties;
    vi. arterial-pressure-wave (pulse) transit time (PTT);
    vii. arterial-pressure-wave velocity;
    viii. an individual's baseline values of said parameters;
    ix. characteristics of displacement of said parameters from baseline values;
    x. the magnitude, range, speed, time length, and pattern of temporal changes in said parameters;
    xi. the magnitude, range, speed, time length, and pattern of spatial changes in said parameters with respect to different anatomical locations;
    xii. augmentation index (AI);
    xiii. a functional relationship between at least two reference values;
    xiv. at least one measure of similarity with at least one typical value for an individual;
    xv. at least one measure of difference with an individual's baseline (typical) values;
    xvi. at least one measure of similarity with at least one typical pattern for an individual;
    xvii. at least one measure of similarity with at least one typical value for a population;
    xviii. at least one measure of difference with at least one typical pattern for a population;
    xix. at least one measure of similarity with at least one typical pattern for a population;
    xx. a functional relationship between said parameters and at least two reference points within at least one reference signal selected from:
        a. systolic pressure;
        b. diastolic pressure;
        c. mean arterial pressure:
        d. heart rate;
        e. arterial-pressure-wave (pulse) transit time;
        f. arterial-pressure-wave velocity; and
        g. vascular properties:
    xxi. a functional relationship between said parameters and at least two reference values within at least two said reference signals.

4. A method as set forth in claim 1 which includes tracking the passage of pressure waves in at least one central artery selected from: the aorta, ascending aorta, thoracic aorta, abdominal aorta, pulmonary artery, renal arteries, carotid arteries, and subclavian arteries.

5. A method as set forth in claim 1 in which at least one sensor is placed in the vicinity of a non-central artery to obtain a signal related to the blood-pressure wave in the non-central artery in order to compare said signal with that registered in the vicinity of a central artery, and to separate peripheral vascular activity from the systemic blood pressure.

6. A method as set forth in claim 1 in which said at least two sensors include at least one sensor selected from: a MEMS sensor, a three-axial MEMS accelerometer sensor, electrocardiographic sensor, photoplethysmographic sensor, impedance plethysmography sensor, ultrasound sensor, and volume-clamp sensor and
    in which said processing includes determining said at least two parameters of cardiovascular activity in at least one data type selected from:
    A. Electrocardiogram (ECG):
    B. Accelerations of the torso surface registered by said at least one sensor, which contains an accelerometer;
    C. Pressure-wave signal;
    D. The $1^{st}$ derivative (acceleration) of the pressure wave registered by said at least one sensor, which contains an accelerometer; and
    E. The $2^{nd}$ derivative of the pressure wave signal registered by said at least one sensor, which contains an accelerometer;
    wherein said at least two parameters of cardiovascular activity are selected from:
    i. the amplitude of the specific peaks,
    ii. the area of the specific peaks,
    iii. the duration of the specific peaks,
    iv. the time of occurrence of the specific peaks,
    v. the median, mode, standard deviation, variance, and range of temporal variation of the systolic, diastolic, and mean arterial pressure;

vi. space-time maps of at least one distribution of the signal parameters listed above in at least two said signals:
vii. the time of the fiducial points, including at least one parameter selected from: the peak of the ECG R, P, O, S, T, and U wave; the beginning, peak, and end of the pressure wave: the beginning, peak, and end of the pressure-wave acceleration; and the beginning, peak, and end of the pressure-wave $2^{nd}$ derivative:

and further includes determining said at least one parameter of cardiovascular mechanical activity related to the arterial pressure in the central arteries, wherein said at least one parameter is selected from:
i. the time interval between the specific peaks in at least one said signal;
ii. the time interval between the time of occurrence of at least one specific peak in at least two said signals;
iii. pressure-wave velocity;
iv. arterial-pressure-wave (pulse) transit time;
v. systolic pressure;
vi. diastolic pressure;
vii. mean arterial pressure:
viii. heart rate;
ix. vascular properties:
x. the augmentation index.

7. A method as set forth in claim 1 in which at least one of said at least two sensors is placed on at least one site selected from a limb, the torso, the neck, and the head of said subject.

8. A method as set forth in claim 1 which includes:
placing at least two accelerometer-containing sensors adapted for measuring at least one movement related to cardiovascular mechanical activity, at specific locations on the surface of an individual's torso;
monitoring physiological signals;
preprocessing said physiological signals respecting the heart's mechanical activity to separate signals from noise and interference; and
processing said physiological signals to determine at least one parameter value and to track the passage of the arterial blood-pressure wave through said at least two sensors' locations.

9. A system for dynamic evaluation of at least one indicator selected from arterial pressure, cardiac output, and vascular properties, said system comprising:
at least two sensors, at least one of which is adapted for placement on the surface of an individual's torso, contains an accelerometer, and is further adapted for registering torso-surface movement related to cardiovascular mechanical activity;
an acquisition module for acquiring information from said at least two sensors; and
a processing module for processing said information (signal) from said at least two sensors wherein said processing module is adapted to determine at least two parameters of cardiovascular activity and is further adapted to derive at least one parameter of cardiovascular mechanical activity related to the arterial pressure in the central arteries.

10. A system as set forth in claim 9 in which said sensors include at least two MEMS sensors.

11. A system as set forth in claim 9 which includes filters to improve the signal-to-noise ratio with respect to the arterial pressure-wave signal and to reduce the impact of at least one type of interference selected from: power-line interference, noise, artifacts, and electromagnetic interference, using at least one component selected from: a fixed filter, adaptive filter, pattern-recognition component, orthogonal linear decomposition component, and wavelet decomposition component.

12. A system as set forth in claim 9 which further includes a communication module for communicating with at least one of the following devices: external computer, computer tablet, smart phone, and Internet cloud.

13. A system as set forth in claim 9 which includes an output/display module.

14. A system as set forth in claim 9 in which said at least two sensors include at least one sensor-is-selected from an electrocardiographic sensor, accelerometer, photoplethysmographic sensor, impedance plethysmography sensor, MEMS sensor, three-axial MEMS sensor, ultrasound sensor, and volume-clamp sensor; and in which said processing module performs at least one of the following processing steps:
determining said at least two parameters of cardiovascular activity in at least one said signal selected from:
A. Electrocardiogram (ECG):
B. Acceleration of the torso surface registered by said at least one sensor, which contains an accelerometer;
C. Pressure-wave signal;
D. The $1^{st}$ derivative (acceleration) of the pressure wave registered by said at least one sensor, which contains an accelerometer; and
E. The $2^{nd}$ derivative of the pressure wave registered by said at least one sensor, which contains an accelerometer;
wherein said at least two parameters of cardiovascular activity are selected from:
i. the amplitude of the specific peaks;
ii. the area of the specific peaks;
iii. the duration of the specific peaks;
iv. the time of occurrence of the specific peaks;
v. the median, mode, standard deviation, variance, and range of temporal variation of the systolic, diastolic, and mean arterial pressure:
vi. space-time maps of at least one distribution of the signal parameters listed above in at least two said signals;
vii. the time of the fiducial points, including at least one parameter selected from: the peak of the ECG R, P, O, S, T, and U wave; the beginning, peak, and end of the pressure wave; the beginning, peak, and end of the pressure-wave acceleration; and the beginning, peak, and end of the pressure-wave $2^{nd}$ derivative;
and further determining said at least one parameter of cardiovascular mechanical activity related to the arterial pressure in the central arteries, wherein said at least one parameter is selected from:
i. the time intervals between the specific peaks in at least one said signal;
ii. the time intervals between the time of occurrence of at least one specific peak in at least two said signals;
iii. pressure-wave velocity;
iv. arterial-pressure-wave (pulse) transit time
v. systolic pressure;
vi. diastolic pressure;
vii. mean arterial pressure;
viii. heart rate;
ix. vascular properties;
x. the augmentation index.

15. A system as set forth in claim 12, in which said communication module is wireless.

16. A system as set forth in claim 9 in which said at least one sensor includes a combination of at least one accelerometer and at least one electrocardiographic sensor.

17. A system as set forth in claim 9 in which said processing module is further adapted to perform calibration of said information using at least one reference selected from:
   i. systolic pressure;
   ii. diastolic pressure;
   iii. mean arterial pressure;
   iv. heart rate;
   v. vascular properties;
   vi. arterial-pressure-wave (pulse) transit time;
   vii. arterial-pressure-wave velocity;
   viii. an individual's baseline values;
   ix. characteristics of displacement from baseline values;
   x. the magnitude, range, speed, time length, and pattern of temporal changes;
   xi. the magnitude, range, speed, time length, and pattern of spatial changes with respect to different anatomical locations;
   xii. augmentation index;
   xiii. a functional relationship between at least two reference values;
   xiv. at least one measure of similarity with an individual's baseline (typical) values;
   xv. at least one measure of difference with an individual's baseline values;
   xvi. at least one measure of similarity with at least one typical pattern for an individual;
   xvii. at least one measure of similarity with at least one baseline value in a group of subjects;
   xviii. at least one measure of difference with group baseline values in a group of subjects;
   xix. at least one measure of similarity with at least one typical pattern for a group of subjects;
   xx. a functional relationship between said parameters and at least two reference points within at least one reference signal selected from:
      a. systolic pressure;
      b. diastolic pressure;
      c. mean arterial pressure;
      d. heart rate;
      e. arterial-pressure-wave (pulse) transit time;
      f. arterial-pressure-wave velocity;
      g. vascular properties;
   xxi. a functional relationship between said parameters and at least two reference points in at least two said reference signals.

18. A system as set forth in claim 9, which includes:
   (i) at least two accelerometer-containing sensors, which are adapted for placement on the surface of an individual's torso and for measuring mechanical movement related to cardiovascular mechanical activity;
   (ii) at least one acquisition module for receiving information from said at least two sensors; and
   (iii) at least one processing module for processing said at least two signals obtained from said two sensors, with said processing adapted for determining at least one parameter value related to cardiovascular activity and further adapted for tracking at least one parameter of cardiovascular mechanical activity measured by at least two said sensors containing accelerometers.

19. A system for dynamic evaluation of at least one indicator selected from arterial pressure, cardiac output, and vascular properties, said system comprising:
   at least two accelerometer-containing MEMS sensors adapted for placement on the surface of an individual's torso and further adapted for measuring torso-surface movement related to cardiovascular mechanical activity;
   at least one acquisition module for receiving information (data) from said at least two sensors; and
   at least one processing module for processing said information from said at least two sensors wherein said processing module is adapted to determine at least two parameters of cardiovascular activity and is further adapted to derive at least one parameter of cardiovascular mechanical activity related to the arterial pressure in the central arteries.

20. A system as set forth in claim 19 which further includes a communication module for communicating with at least one of the following devices: external computer, computer tablet, smart phone, and Internet cloud.

21. A system as set forth in claim 20 in which said communication module is wireless.

22. A system as set forth in claim 19 which further includes at least one sensor selected from: an electrocardiographic sensor, photoplethysmographic sensor, impedance plethysmography sensor, accelerometer sensor, a MEMS sensor, a three-axial MEMS accelerometer sensor, ultrasound sensor, and volume-clamp sensor; and in which said processing module contains at least one functional element that performs at least one of the following operations:
   (i) determining said at least two parameters of cardiovascular activity from at least one data type selected from:
      A. Electrocardiogram (ECG);
      B. Acceleration of the torso surface registered by said at least one sensor, which contains an accelerometer;
      C. Pressure-wave signal;
      D. The $1^{st}$ derivative (acceleration) of the pressure wave registered by said at least one sensor, which contains an accelerometer; and
      E. The $2^{nd}$ derivative of the pressure wave registered by said at least one sensor, which contains an accelerometer;
      wherein said at least two parameters of cardiovascular activity are selected from:
         i. the amplitude of the specific peaks;
         ii. the area of the specific peaks;
         iii. the duration of the specific peaks;
         iv. the time of occurrence of the specific peaks;
         v. the median, mode, standard deviation, variance, and range of temporal variation of the systolic, diastolic, and mean arterial pressure;
         vi. space-time maps of at least one distribution of the signal parameters listed above in at least two said signals;
         vii. the time of the fiducial points, including at least one parameter selected from: the peak of the ECG R, P, Q, S, T, and U wave; the beginning, peak, and end of the pressure wave; the beginning, peak, and end of the pressure-wave acceleration; and the beginning, peak, and end of the pressure-wave $2^{nd}$ derivative;
   and further determining said at least one parameter of cardiovascular mechanical activity related to the arterial pressure in the central arteries, wherein said at least one parameter is selected from:
      i. the time intervals between the specific peaks in at least one said signal;
      ii. the time intervals between the time of occurrence of at least one specific peak in at least two said signals;

iii. pressure-wave velocity;
iv. arterial-pressure-wave (pulse) transit time;
v. systolic pressure;
vi. diastolic pressure;
vii. mean arterial pressure;
viii. heart rate;
ix. vascular properties;
x. the augmentation index;
(ii) calibrating said parameters with respect to at least one reference value selected from:
i. systolic pressure;
ii. diastolic pressure;
iii. mean arterial pressure;
iv. heart rate;
v. vascular properties;
vi. arterial-pressure-wave (pulse) transit time;
vii. arterial-pressure-wave velocity;
viii. an individual's baseline values;
ix. characteristics of displacement from baseline values;
x. the magnitude, range, speed, time length, and pattern of temporal changes;
xi. the magnitude, range, speed, time length, and pattern of spatial changes with respect to different anatomical locations;
xii. augmentation index;
xiii. a functional relationship between at least two reference values;
xiv. at least one measure of similarity with an individual's baseline (typical) values;
xv. at least one measure of difference with an individual's baseline values;
xvi. at least one measure of similarity with at least one typical pattern for an individual;
xvii. at least one measure of similarity with at least one baseline value in a group of subjects;
xviii. at least one measure of difference with group baseline values in a group of subjects;
xix. at least one measure of similarity with at least one typical pattern for a group of subjects;
xx. a functional relationship between said parameters and at least two reference points within at least one reference signal selected from:
a. systolic pressure;
b. diastolic pressure;
c. mean arterial pressure;
d. heart rate;
e. arterial-pressure-wave (pulse) transit time;
f. arterial-pressure-wave velocity;
g. vascular properties;
xxi. a functional relationship between said parameters and at least two reference points in at least two said reference signals.

23. A system as set forth in claim 19 in which at least one of said at least two sensors is placed on at least one site selected from a limb, the torso, the neck, and the head of said subject.

24. A system for monitoring at least one vital sign selected from blood pressure, cardiac output, and vascular activity, said system comprising:
at least one accelerometer-containing sensor adapted for registering at least one mechanical movement of the surface of the torso;
at least one acquisition module for acquiring information (data) from said at least one sensor over multiple cardiac cycles; and
at least one processing module adapted to process said information respecting the features that originate from at least two anatomical locations using at least one processing step selected from:
(i) determining said at least two parameters of cardiovascular activity in at least one data type selected from:
A. Electrocardiogram (ECG);
B. Accelerations of the torso surface registered by said at least one sensor, which contains an accelerometer;
C. Pressure-wave signal;
D. The $1^{st}$ derivative (acceleration) of the pressure wave registered by said at least one sensor, which contains an accelerometer; and
E. The $2^{nd}$ derivative of the pressure wave registered by said at least one sensor, which contains an accelerometer;
wherein said at least two parameters of cardiovascular activity are selected from:
i. the amplitude of the specific peaks;
ii. the area of the specific peaks;
iii. the duration of the specific peaks;
iv. the time of occurrence of the specific peaks;
v. the median, mode, standard deviation, variance, and range of temporal variation of the systolic, diastolic, and mean arterial pressure;
vi. space-time maps of at least one distribution of the signal parameters listed above in at least two said signals;
vii. the time of the fiducial points, including at least one parameter selected from: the peak of the ECG R, P, Q, S, T,
and U wave; the beginning, peak, and end of the pressure wave; the beginning, peak, and end of the pressure-wave acceleration; and the beginning, peak, and end of the pressure-wave $2^{nd}$ derivative;
and further determining said at least one parameter of cardiovascular mechanical activity related to the arterial pressure in the central arteries, wherein said at least one parameter is selected from:
i. the time intervals between the specific peaks in at least one said signal,
ii. the time intervals between the time of occurrence of at least one specific peak in at least two said signals;
iii. pressure-wave velocity;
iv. arterial-pressure-wave (pulse) transit time;
v. systolic pressure;
vi. diastolic pressure;
vii. mean arterial pressure;
viii. heart rate;
ix. vascular properties;
x. the augmentation index;
(ii) calibrating said parameters with respect to at least one reference selected from:
i. systolic pressure;
ii. diastolic pressure;
iii. mean arterial pressure;
iv. heart rate;
v. vascular properties;
vi. arterial-pressure-wave (pulse) transit time;
vii. arterial-pressure-wave velocity;
viii. an individual's baseline values;
ix. characteristics of displacement from baseline values;
x. the magnitude, range, speed, time length, and pattern of temporal changes;
xi. the magnitude, range, speed, time length, and pattern of spatial changes with respect to different anatomical locations;

xii. augmentation index;
xiii. a functional relationship between at least two reference values;
xiv. at least one measure of similarity with an individual's baseline (typical) values;
xv. at least one measure of difference with an individual's baseline values;
xvi. at least one measure of similarity with at least one typical pattern for an individual;
xvii. at least one measure of similarity with at least one baseline value in a group of subjects;
xviii. at least one measure of difference with group baseline values in a group of subjects;
xix. at least one measure of similarity with at least one typical pattern for a group of subjects;
xx. a functional relationship between said parameters and at least two reference points within at least one reference signal selected from:
  a. systolic pressure;
  b. diastolic pressure;
  c. mean arterial pressure;
  d. heart rate;
  e. arterial-pressure-wave (pulse) transit time;
  f. arterial-pressure-wave velocity;
  g. vascular properties;
xxi. a functional relationship between said parameters and at least two reference points in at least two said reference signals.

25. A system as set forth in claim 24 which further includes at least one sensor which is placed on at least one site selected from a limb, the torso, the neck, and the head of said subject.

26. A system as set forth in claim 24 which further includes at least one sensor selected from: an electrocardiographic sensor, photoplethysmographic sensor, impedance plethysmography sensor, accelerometer sensor, a MEMS sensor, a three-axial MEMS accelerometer sensor, ultrasound sensor, and volume-clamp sensor.

27. A device for monitoring at least one vital sign selected from blood pressure, cardiac output, and vascular activity, said device comprising:
  at least two sensors, at least one of which is adapted for placement on the surface of an individual's torso, contains an accelerometer, and is further adapted for measuring torso-surface movement related to cardiovascular mechanical activity;
  at least one acquisition module for acquiring information (data) from said at least two sensors over multiple cardiac cycles;
  at least one module selected from communication module and data-storage (memory) module for transferring said information to an external processing module wherein said processing module is adapted to determine at least two parameters of cardiovascular activity and is further adapted to derive at least one parameter of cardiovascular mechanical activity related to the arterial pressure in the central arteries.

28. A portable device as set forth in claim 27 which further includes at least one sensor selected from: an electrocardiographic sensor, photoplethysmographic sensor, impedance plethysmography sensor, accelerometer sensor, a MEMS sensor, a three-axial MEMS accelerometer sensor, ultrasound sensor, and volume-clamp sensor.

29. A portable device as set forth in claim 27, in which said processing module is further adapted to include at least one functional element that performs at least one of the following operations:
(i) determining said at least two parameters of cardiovascular activity in at least one data type selected from:
  A. Electrocardiogram (ECG);
  B. Acceleration of the torso surface registered by said at least one sensor, which contains an accelerometer;
  C. Pressure-wave signal;
  D. The $1^{st}$ derivative (acceleration) of the pressure wave registered by said at least one sensor, which contains an accelerometer; and
  E. The $2^{nd}$ derivative of the pressure wave registered by said at least one sensor, which contains an accelerometer;
  wherein said at least two parameters of cardiovascular activity are selected from:
    i. the amplitude of the specific peaks;
    ii. the area of the specific peaks;
    iii. the duration of the specific peaks;
    iv. the time of occurrence of the specific peaks;
    v. the median, mode, standard deviation, variance, and range of temporal variation of the systolic, diastolic, and mean arterial pressure;
    vi. space-time maps of at least one distribution of the signal parameters listed above in at least two said signals;
    vii. the time of the fiducial points, including at least one parameter selected from: the peak of the ECG R, P, Q, S, T, and U wave; the beginning, peak, and end of the pressure wave; the beginning, peak, and end of the pressure-wave acceleration; and the beginning, peak, and end of the pressure-wave $2^{nd}$ derivative;
  and further determining said at least one parameter of cardiovascular mechanical activity related to the arterial pressure in the central arteries, wherein said at least one parameter is selected from:
    i. the time intervals between the specific peaks in at least one said signal;
    ii. the time intervals between the time of occurrence of at least one specific peak in at least two said signals;
    iii. pressure-wave velocity;
    iv. arterial-pressure-wave (pulse) transit time;
    v. systolic pressure;
    vi. diastolic pressure;
    vii. mean arterial pressure;
    viii. heart rate;
    ix. vascular properties;
    x. the augmentation index;
(ii) calibrating said parameters with respect to at least one reference selected from:
  i. systolic pressure;
  ii. diastolic pressure;
  iii. mean arterial pressure;
  iv. heart rate;
  v. vascular properties;
  vi. arterial-pressure-wave (pulse) transit time;
  vii. arterial-pressure-wave velocity;
  viii. an individual's baseline values;
  ix. characteristics of displacement from baseline values;
  x. the magnitude, range, speed, time length, and pattern of temporal changes;
  xi. the magnitude, range, speed, time length, and pattern of spatial changes with respect to different anatomical locations;
  xii. augmentation index;
  xiii. a functional relationship between at least two reference values;

xiv. at least one measure of similarity with an individual's baseline (typical) values;
xv. at least one measure of difference with an individual's baseline values;
xvi. at least one measure of similarity with at least one typical pattern for an individual;
xvii. at least one measure of similarity with at least one baseline value in a group of subjects;
xviii. at least one measure of difference with group baseline values in a group of subjects;
xix. at least one measure of similarity with at least one typical pattern for a group of subjects;
xx. a functional relationship between said parameters and at least two reference points within at least one reference signal selected from:
  a. systolic pressure;
  b. diastolic pressure;
  c. mean arterial pressure;
  d. heart rate;
  e. arterial-pressure-wave (pulse) transit time;
  f. arterial-pressure-wave velocity;
  g. vascular properties;
xxi. a functional relationship between said parameters and at least two reference points in at least two said reference signals.

30. A portable device as set forth in claim 27 in which at least one of said at least two sensors is placed on at least one site selected from a limb, the torso, the neck, and the head of said subject.

31. A portable device as set forth in claim 27 in which said communication module is adapted for communicating with at least one of the following devices: external computer, computer tablet, smart phone, and Internet cloud.

32. A portable device as set forth in claim 31 in which said communication module is wireless.

33. A portable device as set forth in claim 27, which includes:
  (i) at least two accelerometer-containing sensors, which are adapted for placement on the surface of an individual's torso and for registering mechanical movement related to cardiovascular mechanical activity;
  (ii) an acquisition module for receiving information from said at least two sensors over multiple cardiac cycles; and
  (iii) at least one module selected from communication module and data-storage (memory) module for transferring said information to an external processing module wherein said processing module is adapted to determine at least two parameter values of cardiovascular activity registered by at least two said sensors containing accelerometers.

34. A device as set forth in claim 27, which is adapted for incorporation into a patch for attachment on the skin surface of an individual's torso.

35. A device as set forth in claim 34, said device further adapted to have an adhesive substance on its cover to provide good attachment to the skin surface.

36. A device as set forth in claim 27, which is adapted for incorporation into at least one portable unit selected from: a Holter ECG monitor, body-surface patch, bag, pack, wristband, belt, vest, t-shirt, necklace, headband, armchair, car seat, bed, and mattress.

* * * * *